(12) United States Patent
Pacetti (10) Patent No.: US 9,180,225 B2
(45) Date of Patent: *Nov. 10, 2015

(54) IMPLANTABLE MEDICAL DEVICES WITH A TOPCOAT LAYER OF PHOSPHORYL CHOLINE ACRYLATE POLYMER FOR REDUCED THROMBOSIS, AND IMPROVED MECHANICAL PROPERTIES

(75) Inventor: Stephen D. Pacetti, San Jose, CA (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/597,600

(22) Filed: Aug. 29, 2012

(65) Prior Publication Data

US 2012/0330405 A1 Dec. 27, 2012

Related U.S. Application Data

(62) Division of application No. 11/803,651, filed on May 14, 2007.

(51) Int. Cl.
| | | |
|---|---|---|
| *A61F 2/00* | (2006.01) | |
| *C08F 20/58* | (2006.01) | |
| *C08F 20/38* | (2006.01) | |
| *C08F 22/38* | (2006.01) | |
| *C08F 118/02* | (2006.01) | |
| *C08F 120/58* | (2006.01) | |
| *C08F 120/70* | (2006.01) | |
| *C08F 122/38* | (2006.01) | |
| *C08F 220/54* | (2006.01) | |
| *C08F 220/10* | (2006.01) | |
| *A61L 27/54* | (2006.01) | |
| *A61L 27/34* | (2006.01) | |
| *A61L 31/10* | (2006.01) | |
| *A61L 31/16* | (2006.01) | |

(52) U.S. Cl.
CPC .............. *A61L 27/54* (2013.01); *A61L 27/34* (2013.01); *A61L 31/10* (2013.01); *A61L 31/16* (2013.01); *A61L 2300/41* (2013.01); *A61L 2300/416* (2013.01); *A61L 2300/42* (2013.01); *A61L 2300/606* (2013.01); *A61L 2420/08* (2013.01)

(58) Field of Classification Search
None
See application file for complete search history.

(56) References Cited

U.S. PATENT DOCUMENTS

| | | | |
|---|---|---|---|
| 2,458,420 A | * | 1/1949 | Reynolds et al. ............. 526/304 |
| 4,141,874 A | | 2/1979 | Oka et al. |
| 4,157,418 A | * | 6/1979 | Heilmann ............. 428/355 CN |
| 4,172,934 A | | 10/1979 | Heilmann |
| 4,668,506 A | | 5/1987 | Bawa |
| 4,792,599 A | | 12/1988 | Durrani |
| 4,931,287 A | | 6/1990 | Bae et al. |
| 5,010,121 A | | 4/1991 | Yeates et al. |
| 5,019,096 A | | 5/1991 | Fox, Jr. et al. |
| 5,155,252 A | | 10/1992 | Yamamoto et al. |
| 5,163,952 A | | 11/1992 | Froix |
| 5,258,020 A | | 11/1993 | Froix |
| 5,496,581 A | | 3/1996 | Yianni et al. |
| 5,607,467 A | | 3/1997 | Froix |
| 5,616,338 A | | 4/1997 | Fox, Jr. et al. |
| 5,674,242 A | | 10/1997 | Phan et al. |
| 5,717,047 A | | 2/1998 | Russell et al. |
| 5,723,219 A | | 3/1998 | Kolluri et al. |
| 5,780,559 A | | 7/1998 | Humbert et al. |
| 5,783,650 A | | 7/1998 | Bowers et al. |
| 5,824,049 A | | 10/1998 | Ragheb et al. |
| 5,859,174 A | | 1/1999 | Barancyk et al. |
| 5,873,904 A | | 2/1999 | Ragheb et al. |
| 5,879,713 A | | 3/1999 | Roth et al. |
| 5,908,704 A | | 6/1999 | Friedman et al. |
| 5,932,299 A | | 8/1999 | Katoot |
| 5,962,138 A | | 10/1999 | Kolluri et al. |
| 5,997,517 A | | 12/1999 | Whitbourne |
| 6,083,257 A | | 7/2000 | Taylor et al. |
| 6,087,462 A | | 7/2000 | Bowers et al. |
| 6,090,901 A | | 7/2000 | Bowers et al. |
| 6,096,070 A | | 8/2000 | Ragheb et al. |
| 6,110,483 A | | 8/2000 | Whitbourne et al. |
| 6,143,354 A | | 11/2000 | Koulik et al. |
| 6,150,432 A | | 11/2000 | Jones et al. |
| 6,159,978 A | | 12/2000 | Myers et al. |
| 6,165,338 A | | 12/2000 | December et al. |
| 6,180,632 B1 | | 1/2001 | Myers et al. |
| 6,214,901 B1 | | 4/2001 | Chudzik et al. |
| 6,225,431 B1 | | 5/2001 | Bowers et al. |
| 6,245,760 B1 | | 6/2001 | He et al. |
| 6,248,129 B1 | | 6/2001 | Froix |
| 6,258,371 B1 | | 7/2001 | Koulik et al. |

(Continued)

FOREIGN PATENT DOCUMENTS

| | | |
|---|---|---|
| EP | 0 947205 | 10/1999 |
| JP | 08-059950 | 3/1996 |

(Continued)

OTHER PUBLICATIONS

Nakayama et al. Journal of Biomedical Materials Research Part B Applied Biomaterials 2007 80B:260-267.*

(Continued)

*Primary Examiner* — Juliet Switzer
*Assistant Examiner* — Caralynne Helm
(74) *Attorney, Agent, or Firm* — Squire Patton Boggs (US) LLP (57) ABSTRACT

The present invention relates to implantable medical devices coated with phosphoryl choline acrylate polymer topcoat layer and their use in the treatment of vascular diseases.

15 Claims, 2 Drawing Sheets

(56) References Cited

U.S. PATENT DOCUMENTS

| | | |
|---|---|---|
| 6,262,034 B1 | 7/2001 | Mathiowitz et al. |
| 6,270,788 B1 | 8/2001 | Koulik et al. |
| 6,277,449 B1 | 8/2001 | Kolluri et al. |
| 6,287,707 B1 | 9/2001 | Luthra et al. |
| 6,299,604 B1 | 10/2001 | Ragheb et al. |
| 6,306,176 B1 | 10/2001 | Whitbourne |
| 6,329,386 B1 | 12/2001 | Mollison |
| 6,344,035 B1 | 2/2002 | Chudzik et al. |
| 6,383,196 B1 | 5/2002 | Bates et al. |
| 6,387,379 B1 | 5/2002 | Goldberg et al. |
| 6,419,711 B1 | 7/2002 | Genet et al. |
| 6,475,779 B2 | 11/2002 | Mathiowitz et al. |
| 6,482,834 B2 | 11/2002 | Spada et al. |
| 6,524,347 B1 | 2/2003 | Myers et al. |
| 6,528,526 B1 | 3/2003 | Myers et al. |
| 6,530,950 B1 | 3/2003 | Alvarado et al. |
| 6,530,951 B1 | 3/2003 | Bates et al. |
| 6,613,432 B2 | 9/2003 | Zamora et al. |
| 6,620,617 B2 | 9/2003 | Mathiowitz et al. |
| 6,663,662 B2 | 12/2003 | Pacetti et al. |
| 6,706,819 B1 | 3/2004 | Araki et al. |
| 6,730,064 B2 | 5/2004 | Ragheb et al. |
| 6,776,796 B2 | 8/2004 | Falotico et al. |
| 6,790,228 B2 | 9/2004 | Hossainy et al. |
| 6,890,583 B2 | 5/2005 | Chudzik et al. |
| 7,005,137 B1 | 2/2006 | Hossainy et al. |
| 7,008,667 B2 | 3/2006 | Chudzik et al. |
| 7,077,859 B2 | 7/2006 | Sirhan et al. |
| 7,094,256 B1 | 8/2006 | Shah et al. |
| 7,217,426 B1 | 5/2007 | Hossainy |
| 7,247,313 B2 | 7/2007 | Roorda et al. |
| 7,357,942 B2 | 4/2008 | Burke et al. |
| 7,396,539 B1 | 7/2008 | Hossainy et al. |
| 7,485,141 B2 | 2/2009 | Majercak et al. |
| 7,560,492 B1 | 7/2009 | Claude et al. |
| 7,563,454 B1 | 7/2009 | Pacetti |
| 7,618,937 B2 | 11/2009 | Messersmith et al. |
| 7,622,533 B2 | 11/2009 | Lee |
| 7,622,537 B2 | 11/2009 | Pacetti |
| 7,700,659 B2 | 4/2010 | Pacetti |
| 7,713,541 B1 | 5/2010 | Pacetti et al. |
| 7,781,551 B2 | 8/2010 | Pacetti et al. |
| 7,910,678 B2 | 3/2011 | Pacetti |
| 7,928,176 B2 | 4/2011 | Pacetti |
| 7,928,177 B2 | 4/2011 | Pacetti |
| 7,974,307 B2 | 7/2011 | Meric |
| 2001/0007083 A1 | 7/2001 | Roorda |
| 2001/0029351 A1 | 10/2001 | Falotico et al. |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0051730 A1 | 5/2002 | Bodnar et al. |
| 2002/0082679 A1 | 6/2002 | Sirhan et al. |
| 2002/0111590 A1 | 8/2002 | Davila et al. |
| 2002/0133183 A1 | 9/2002 | Lentz et al. |
| 2002/0165608 A1 | 11/2002 | Llanos et al. |
| 2002/0176849 A1 | 11/2002 | Slepian |
| 2002/0188037 A1 | 12/2002 | Chudzik et al. |
| 2003/0004141 A1 | 1/2003 | Brown |
| 2003/0028243 A1 | 2/2003 | Bates et al. |
| 2003/0036794 A1 | 2/2003 | Ragheb et al. |
| 2003/0039689 A1 | 2/2003 | Chen et al. |
| 2003/0040790 A1 | 2/2003 | Furst |
| 2003/0060877 A1 | 3/2003 | Falotico et al. |
| 2003/0065377 A1 | 4/2003 | Davila et al. |
| 2003/0083739 A1 | 5/2003 | Cafferata |
| 2004/0034408 A1 | 2/2004 | Majercak et al. |
| 2004/0117006 A1* | 6/2004 | Lewis et al. .......... 623/1.42 |
| 2005/0080212 A1 | 4/2005 | Jing et al. |
| 2005/0147647 A1* | 7/2005 | Glauser et al. .......... 424/426 |
| 2005/0208093 A1 | 9/2005 | Glauser et al. |
| 2005/0238686 A1 | 10/2005 | Hossainy et al. |
| 2006/0062824 A1 | 3/2006 | Pacetti et al. |
| 2006/0216326 A1 | 9/2006 | Pacetti |
| 2007/0010623 A1 | 1/2007 | Ha |
| 2007/0051531 A1 | 3/2007 | Borgaonkar et al. |
| 2008/0118541 A1 | 5/2008 | Pacetti |
| 2008/0124450 A1 | 5/2008 | Pacetti |
| 2008/0125514 A1 | 5/2008 | Pacetti |
| 2008/0125560 A1 | 5/2008 | Pacetti |
| 2008/0139746 A1 | 6/2008 | Pacetti |
| 2008/0146696 A1 | 6/2008 | Pacetti |
| 2008/0147178 A1 | 6/2008 | Pacetti et al. |
| 2008/0153923 A1 | 6/2008 | Pacetti |
| 2008/0220046 A1 | 9/2008 | Cheng et al. |
| 2008/0286332 A1 | 11/2008 | Pacetti |
| 2009/0060970 A1 | 3/2009 | Toner et al. |
| 2011/0129514 A1 | 6/2011 | Hossainy et al. |
| 2011/0160391 A1 | 6/2011 | Pacetti |

FOREIGN PATENT DOCUMENTS

| | | | |
|---|---|---|---|
| JP | 08059950 A | * | 3/1996 |
| WO | WO 98/22517 | | 5/1998 |
| WO | WO 99/08729 | | 2/1999 |
| WO | WO 2005/092406 | | 10/2005 |

OTHER PUBLICATIONS

Haas et al. Journal of Polymer Science 1959 37:317-319.*
Haas et al. Journal of Polymer Science 1967 5:915-927.*
Iwakura et al. Journal of Polymer Science 1967 5:1585-1597.*
U.S. Appl. No. 11/899,740, filed Sep. 6, 2007, Hossainy et al.
International Search Report for PCT/US2008/060110, mailed Sep. 11, 2009, 13 pgs.
Burke et al., "Zotarolimus (ABT-578) eluting stents", Advanced Drug Delivery Rev. 58, pp. 437-446 (2006).
Cutlip "Standardized Consensus Definitions for DES studies: Impact on Reported Event Rates from Clinical Trials". Hot Line Session. Trancatheter Cardiovascular Therapeutics (2006).
Cutlip Presentation Slide from the 2006 Transcatheter Cardiovascular Therapeutics Meeting held in Washington DC. named "Cumulative Incidence of Stent Thrombosis" (2006).
Lewis et al., "Phosphorylcholine-based polymer coatings for stent drug delivery", J. of Mat. Science 12, pp. 865-870 (2001).
Lewis et al., Biomaterials 22, pp. 99-111 (2001).
Lewis et al., Biomaterials 25, pp. 3099-3108 (2004).
Peck "TCT: New Definition and Data Make Drug-Eluting Coronary Stents Seem Safer", (2006).
U.S. Appl. No. 10/376,348, filed Feb. 26, 2003, Ding et al.
Dyneon™ Fluorothermoplastics—Product Information (2000).
Huang et al., "Synthesis and Characterization of Self-Assembling Block Copolymers Containing Bioadhesive End Groups", Biomacromolecules 3, pp. 397-406 (2002).
Hull et al. THV Fluoroplastic in Modern Fluoropolymers ed. J Scheirs 1997 p. 257.
Kocakulak et al., "Investigation of Blood Compatibility of PMEA Coated Extracorporeal Circuits", J. of Bioactive and Compatible Polymers vol. 17, pp. 343-356 (2002).
Lee et al., "Synthesis and Gelation of DOPA-Modified Poly(ethylene glycol) Hydrogels", Biomacromolecules 3, pp. 1038-1047 (2002).
Maccone et al. Macromoelcules 33: pp. 1656-1663 (2000).
Sipos et al. Biomacromolecules 6: pp. 2570-2582 (2005).
Tanaka et al., "Blood compatible aspects of poly(2-methoxyethylacrylate) (PMEA)-relationship between protein adsorption and platelet adhesion on PMEA surface", Biomaterials 21, pp. 1471-1481 (2000).
Tecnoflon® P 757 (2003).
Trollsas et al., "Hyperbranched Poly(ε-caprolactone) Derived from Interinsically Branched AB2 Macromonomers", Macromolecules 31, pp. 4390-4395 (1998).
Translation of Japanese Notice of Reasons for Rejection for appl. No. P2010-508476, dispatched Feb. 12, 2013, 6 pgs.
Lewis et al., "Phosphorylcholine-Based Polymer Coatings for Stent Drug Delivery", J. of Mat. Science: Materials in Medicine, vol. 12, Nos. 10-12, pp. 865-870 (2001).

* cited by examiner

IMPLANTABLE MEDICAL DEVICES WITH A TOPCOAT LAYER OF PHOSPHORYL CHOLINE ACRYLATE POLYMER FOR REDUCED THROMBOSIS, AND IMPROVED MECHANICAL PROPERTIES

CROSS-REFERENCE TO RELATED APPLICATION

This application is a divisional application of U.S. patent application Ser. No. 11/803,651, filed on May 14, 2007, and published as United States Patent Application Publication No. 2008-0286332 A1 on Nov. 20, 2008, which is incorporated by reference as if fully set forth, including any drawings, herein.

FIELD OF THE INVENTION

This invention relates to the fields of organic chemistry, polymer science, material science and medical devices. In particular, it relates to a medical device having a phosphoryl choline acrylate polymer topcoat layer for treating vascular diseases.

BACKGROUND OF THE INVENTION

Percutaneous transluminal coronary angioplasty (PTCA) is a common procedure for treating heart disease. A problem associated with the PTCA includes the formation of intimal flaps or torn arterial linings which can collapse and occlude the conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of arterial lining, and to reduce the chance of the development of thrombosis and restenosis, a stent is implanted in the lumen to maintain the vascular patency.

Stents are used not only as a mechanical intervention but also as a vehicle for providing biological therapy. As a mechanical intervention, stents act as scaffoldings, functioning to physically hold open and, if desired, to expand the wall of the passageway. Biological therapy can be achieved by medicating the stents. Medicated stents provide for the local administration of a therapeutic substance at the desired site. Local delivery produces fewer side effects and achieves more favorable results.

However, the use of drug eluting stents (DESs) has resulted in a new problem, late stent thrombosis, the forming of blood clots long after the stent is in place. It was deduced that the formation of blood clots was most likely due to delayed healing which was postulated to be a side-effect of the use of cytostatic drugs.

To address the above situation, stents can be fabricated from materials that are biocompatible, biodegradable and, if desired, bio-absorbable. The goal is for the stent to have a biocompatible coating which demonstrates great safety with regard to stent thrombosis. Ideally, the stent coatings should preferably lower acute and sub-acute thrombosis rates. The coating material selected must not only have sufficient mechanical properties but also show excellent coating integrity. The preceding problem has been at least partially ameliorated by the use of increasingly biocompatible materials and/or biocompatible coating.

What is needed is an implantable medical device that includes a polymer coating which reduces stent thrombosis. While this would be particularly useful with regard to coronary stents, it would also provide substantial benefit to any manner of implantable medical devices. Such implantable medical devices for use as drug delivery systems should also demonstrate excellent mechanical properties when implanted in a patient. The present invention provides such implantable medical devices.

SUMMARY OF THE INVENTION

Thus, in one aspect, the current invention relates to an implantable medical device, comprising:
a device body;
an optional primer layer disposed over the device body;
a drug reservoir layer disposed over the device body or the primer layer, if opted, wherein the drug reservoir layer comprises one or more therapeutic agents; and
a topcoat layer disposed as an outermost layer over the drug reservoir layer, wherein the topcoat layer comprises a phosphoryl choline acrylate polymer.

In an aspect of this invention, the implantable medical device is a stent.

In an aspect of this invention, the phosphoryl choline acrylate polymer comprises poly(2-(methacryloyloxyethyl)-2-(trimethylammoniumethyl)-phosphate, inner salt)-co-(n-dodcylmethacrylate)-co-(hydroxypropylmethacrylate)-co-(3-trimethoxysilyl)-propylmethacrylate).

In an aspect of this invention, the (trimethylammoniumethyl)-phosphate, inner salt)/(n-dodecylmethacrylate)/(hydroxypropylmethacrylate)/(3-trimethoxysilyl)-propylmethacrylate) constituent wt/wt ratio is from about 28.8:50.7:15.3:5.3.

In an aspect of this invention, the phosphoryl choline acrylate polymer is substantially amorphous.

In an aspect of this invention, the drug reservoir layer comprises acrylate or methacrylate polymer.

In an aspect of this invention, the acrylate or methacrylate polymer has an average molecular weight of about 20,000 to about 600,000 daltons.

In an aspect of this invention, the acrylate or methacrylate polymer comprises poly(butyl methacrylate).

In an aspect of this invention, the drug reservoir layer comprises poly(acrylate) or poly(methacrylate) having the formula:

wherein:
m=0.005 to 0.90
n=0.10 to 0.995
m+n=1
x=65 to 6960
$R_1$ and $R_2$ are independently selected from the group consisting of hydrogen and methyl; and,
Hydrocarbon Group is selected from the group consisting of an unsaturated or saturated, branched or straight chain $C_1$ to $C_{16}$ aliphatic, a cycloaliphatic or an aromatic, moiety,
In an aspect of this invention, the Polar Group is selected from the group consisting of an alkyl ether and an amide.

In an aspect of this invention, the alkyl ether is selected from the group consisting of:

2-Methoxyethyloxy  2-Ethoxyethyloxy  1-Methyl-2-methoxyethyloxy

In an aspect of this invention, the amide is selected from the group consisting of:

An aspect of this invention is a method of treating a vascular disease, comprising:
deploying in the vasculature of a patient in need thereof an implantable medical device, wherein the device comprises:
a device body;
an optional primer layer disposed over the device body;
a drug reservoir layer disposed over the device body or the primer layer, if opted,
wherein the drug reservoir layer comprises one or more therapeutic agents; and
a topcoat layer disposed as an outermost layer over the drug reservoir layer, wherein the topcoat layer comprises a phosphoryl choline acrylate polymer.

In an aspect of this invention, the implantable medical device is a stent.

In an aspect of this invention, the phosphoryl choline acrylate polymer comprises poly(2-(methacryloyloxyethyl)-2-(trimethylammoniumethyl)-phosphate, inner salt)-co-(n-dodecylmethacrylate)-co-(hydroxypropylmethacrylate)-co-(3-trimethoxysilyl)-propylmethacrylate).

In an aspect of this invention, the (trimethylammoniumethyl)-phosphate, inner salt)/(n-dodecylmethacrylate)/(hydroxypropylmethacrylate)/(3-trimethoxysilyl)-propylmethacrylate) constituent wt/wt ratio is from about 28.8:50.7:15.3:5.3.

In an aspect of this invention, the phosphoryl choline acrylate polymer is substantially amorphous.

In an aspect of this invention, the drug reservoir layer comprises acrylate or methacrylate polymer.

In an aspect of this invention, the acrylate or methacrylate polymer has an average molecular weight of about 20,000 to about 600,000 Daltons.

In an aspect of this invention, the acrylate or methacrylate polymer comprises poly(butyl methacrylate).

In an aspect of this invention, the drug reservoir layer comprises poly(acrylate) or poly(methacrylate) having the formula:

Wherein:
$m = 0.005$ to $0.90$
$n = 0.10$ to $0.995$
$m + n = 1$
$x = 65$ to $6960$
$R_1$ and $R_2$ are independently selected from the group consisting of hydrogen and methyl; and,
Hydrocarbon Group is selected from the group consisting of an unsaturated or saturated, branched or straight chain $C_1$ to $C_{16}$ aliphatic, a cycloaliphatic or an aromatic moiety.

In aspect of this invention, in the formula immediately above, the Polar Group = is selected from the group consisting of an alkyl ether and an amide.

In an aspect of this invention, the alkyl ether is selected from the group consisting of:

2-Methoxyethyloxy  2-Ethoxyethyloxy  1-Methyl-2-methoxyethyloxy

In an aspect of this invention, the amide is selected from the group consisting of:

In an aspect of this invention, the drug reservoir layer further comprising one or more therapeutic agents.

In an aspect of this invention, the vascular disease is atherosclerosis.

In an aspect of this invention, the vascular disease is restenosis.

In an aspect of this invention, the vascular disease is vulnerable plaque.

In an aspect of this invention, the vascular disease is peripheral vascular disease.

In an aspect of this invention, the vascular disease is late stent thrombosis.

BRIEF DESCRIPTION OF THE DRAWINGS

The figures are provided as examples of certain embodiments of this invention to aid in its understanding and are not intended nor are they to be construed as limiting the scope of the invention in any manner whatsoever.

DETAILED DESCRIPTION OF THE INVENTION

Use of the singular herein includes the plural and visa versa unless expressly stated to be otherwise. That is, "a" and "the" refer to one or more of whatever the word modifies. For example, "a therapeutic agent" includes one such agent, two such agents, etc. Likewise, "the layer" may refer to one, two or more layers and "the polymer" may mean one polymer or a plurality of polymers. By the same token, words such as, without limitation, "layers" and "polymers" would refer to one layer or polymer as well as to a plurality of layers or polymers unless, again, it is expressly stated or obvious from the context that such is not intended.

As used herein, a "hydrocarbons" refers to a chemical entity made up entirely of carbon and hydrogen atoms. Hydrocarbons useful for the purposes of this invention include, but are not limited to, saturated or unsaturated, branched or straight-chain aliphatic moieties, saturated or unsaturated cycloaliphatic moieties and aromatic moieties. An aliphatic moiety of this invention may have from 1 to 16 total carbon atoms in the straight or branched chain, designated herein as $C_1$ to $C_{16}$. A saturatd aliphatic chain contains only single covalent bonds between carbon atoms while an unsaturated aliphatic chain contains one or more double and or triple covalent bonds between carbon atoms. Examples of alkyl groups include, without limitation, methyl, ethyl, n-propyl, isopropyl, n-butyl, sec-butyl, tert-butyl, amyl, tert-amyl, hexyl, hepty, octyl, nonyl, decyl, undecyl, undecyl and dodecyl. Cycloaliphatic moieties are saturated or unsaturated aliphatic moieties in which all or a portion of the carbon chain constitutes one or more rings, each having from 3 to 8 carbon atoms. Examples of cycloaliphatic groups include, without limitation, cyclopropyl, cyclobutyl, cyclopentyl, cyclohexyl and cycloheptyl. As used herin, "aryl" refers to a carbocylic (all carbon) ring or two or more fused rings (rings that share two adjacent carbon atoms) that have a fully delocalized pi-electron system and from 6 to 14 carbon atoms in the ring(s). Examples of aryl groups include, but are not limited to, benzene, naphthalene and azulene.

As used herein, the following graphic representation of a polymer:

refers to a regular alternating, a random or a block, preferably at present random, copolymer. As use herein, the letters "n" and "m" connote mole fractions of the constitutional units Y and Z and n+m=1. The letter "X" connotes sequence multiplicity, that is, the number of repeats of the entity within the outside brackets in the polymer.

As used herein, an "implantable medical device" refers to any type of appliance that is totally or partly introduced, surgically or medically, into a patient's body or by medical intervention into a natural orifice, and which is intended to remain there after the procedure. The duration of implantation may be essentially permanent, i.e., intended to remain in place for the remaining lifespan of the patient; until the device biodegrades; or until it is physically removed. Examples of implantable medical devices include, without limitation, implantable cardiac pacemakers and defibrillators; leads and electrodes for the preceding; implantable organ stimulators such as nerve, bladder, sphincter and diaphragm stimulators, cochlear implants; prostheses, vascular grafts, self-expandable stents, balloon-expandable stents, stent-grafts, grafts, artificial heart valves and cerebrospinal fluid shunts.

An implantable medical device specifically designed and intended solely for the localized delivery of a therapeutic agent is within the scope of this invention.

As used herein, "device body" refers to a fully formed implantable medical with an outer surface to which no coating or layer of material different from that of which the device itself is manufactured has been applied. By "outer surface" is meant any surface however spatially oriented that is in contact with bodily tissue or fluids. A common is example of a "device body" is a BMS, i.e., a bare metal stent, which, as the name implies, is a fully-formed usable stent that has not been coated with a layer of any material different from the metal of which it is made on any surface that is in contact with bodily tissue or fluids. Of course, device body refers not only to BMSs but to any uncoated device regardless of what it is made of.

Implantable medical devices made of virtually any material, i.e., materials presently known to be useful for the manufacture of implantable medical devices and materials that may be found to be so in the future, may be used with a coating of this invention. For example, without limitation, an implantable medical device useful with this invention may be made of one or more biocompatible metals or alloys thereof including, but not limited to, cobalt-chromium alloy (ELGILOY, L-605), cobalt-nickel alloy (MP-35N), 316L stainless steel, high nitrogen stainless steel, e.g., BIODUR 108, nickel-titanium alloy (NITINOL), tantalum, platinum, platinum-iridium alloy, gold and combinations thereof.

Implantable medical devices may also be made of polymers that are biocompatible and biostable or biodegradable, the latter term including bioabsorbable and/or bioerodable.

As used herein, "biocompatible" refers to a polymer that both in its intact, as synthesized state and in its decomposed state, i.e., its degradation products, is not, or at least is minimally, toxic to living tissue; does not, or at least minimally and reparably, injure(s) living tissue; and/or does not, or at least minimally and/or controllably, cause(s) an immunological reaction in living tissue.

Among useful biocompatible, relatively biostable polymers are, without limitation, polyacrylates, polymethacryates, polyureas, polyurethanes, polyolefins, polyvinylhalides, polyvinylidenehalides, polyvinylethers, polyvinylaromatics, polyvinylesters, polyacrylonitriles, alkyd resins, polysiloxanes and epoxy resins.

Biocompatible, biodegradable polymers include naturally-occurring polymers such as, without limitation, collagen, chitosan, alginate, fibrin, fibrinogen, cellulosics, starches, dextran, dextrin, hyaluronic acid, heparin, glycosaminoglycans, polysaccharides and elastin.

One or more synthetic or semi-synthetic biocompatible, biodegradable polymers may also be used to fabricate an implantable medical device useful with this invention. As used herein, a synthetic polymer refers to one that is created wholly in the laboratory while a semi-synthetic polymer refers to a naturally-occurring polymer than has been chemically modified in the laboratory. Examples of synthetic polymers include, without limitation, polyphosphazines, polyphosphoesters, polyphosphoester urethane, polyhydroxyacids, polyhydroxyalkanoates, polyanhydrides, polyesters, polyorthoesters, polyamino acids, polyoxymethylenes, poly(ester-amides) and polyimides.

Blends and copolymers of the above polymers may also be used and are within the scope of this invention. Based on the disclosures herein, those skilled in the art will recognize those implantable medical devices and those materials from which they may be fabricated that will be useful with the coatings of this invention.

At present, preferred implantable medical devices for use with the coatings of this invention are stents.

A stent refers generally to any device used to hold tissue in place in a patient's body. Particularly useful stents, however, are those used for the maintenance of the patency of a vessel in a patient's body when the vessel is narrowed or closed due to diseases or disorders including, without limitation, tumors (m, for example, bile ducts, the esophagus, the trachea/bronchi, etc.), benign pancreatic disease, coronary artery disease, carotid artery disease and peripheral arterial disease such as atherosclerosis, restenosis and vulnerable plaque. Vulnerable plaque (VP) refers to a fatty build-up in an arterial wall thought to be caused by inflammation. The VP is covered by a thin fibrous cap that can rupture leading to blood clot formation. A stent can be used to strengthen the wall of the vessel in the vicinity of the VP and act as a shield against such rupture. A stent can be used in, without limitation, neuro, carotid, coronary, pulmonary, aorta, renal, biliary, iliac, femoral and popliteal as well as other peripheral vasculatures. A stent can be used in the treatment or prevention of disorders such as, without limitation, thrombosis, restenosis, hemorrhage, vascular dissection or perforation, vascular aneurysm, chronic total occlusion, claudication, anastomotic proliferation, bile duct obstruction and ureter obstruction.

In addition to the above uses, stents may also be employed for the localized delivery of therapeutic agents to specific treatment sites in a patient's body. In fact, therapeutic agent delivery may be the sole purpose of the stent or the stent may be primarily intended for another use such as those discussed above with drug delivery providing an ancillary benefit.

A stent used for patency maintenance is usually delivered to the target site in a compressed state and then expanded to fit the vessel into which it has been inserted. Once at a target location, a stent may be self-expandable or balloon expandable. In any event, due to the expansion of the stent, any coating thereon must be flexible and capable of elongation.

Figure 1:
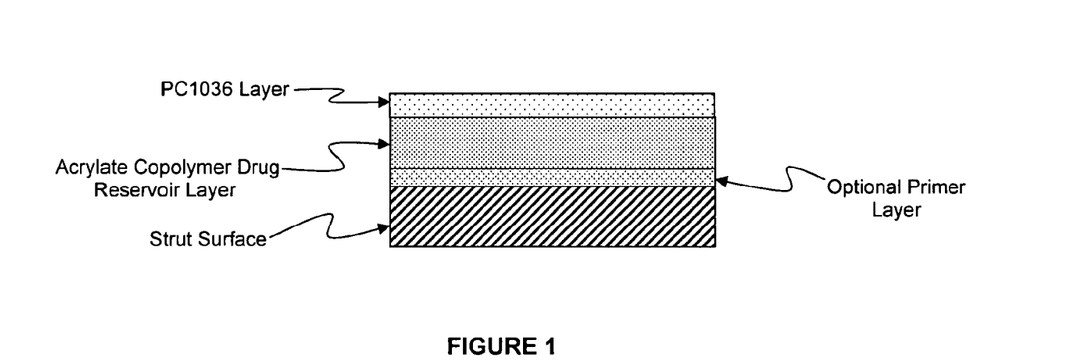
FIG. 1 depicts an embodiment of this invention showing a portion of a stent strut in cross section. The stent coating structure includes a stent body, optional primer layer, drug reservoir layer and the topcoat layer.

FIG. 1 depicts an embodiment of this invention showing stent coating structure which includes stent body, optional primer layer, drug reservoir layer and the topcoat layer.

As used herein, "optional" means that the element modified by the term may or may not be present. For example, without limitation, a device body (db) that has coated on it an "optional" primer layer (pl), a drug reservoir layer (dr), and a top-coat layer (tc) (which it should be noted is not optional herein) refers, without limitation, to any of the following devices: db+pl+dr+tc and db+dr+tc.

As used herein, a "primer layer" refers to a coating consisting of a polymer or blend of polymers that exhibit good adhesion characteristics with regard to the material of which the device body is manufactured and good adhesion characteristic with regard to whatever material is to be coated on the device body. Thus, a primer layer serves as an intermediary layer between a device body and materials to be affixed to the device body and is, therefore, applied directly to the device body. Examples without limitation, of primers include acrylate and methacrylate polymers with poly(n-butyl methacrylate) being a presently preferred primer. Some additional examples of primers include, but are not limited to, poly(ethylene-co-vinyl alcohol), poly(vinyl acetate-co-vinyl alcohol), poly(methacrylates), poly(acrylates), polyethyleneamine, polyallylamine, chitosan, poly(ethylene-co-vinyl acetate), and parylene-C.

As use herein, a material that is described as a layer "disposed over" an indicated substrate, e.g., without limitation, a device body or another layer, refers to a relatively thin coating of the material applied, preferably at present, directly to essentially is the entire exposed surface of the indicated substrate. By "exposed surface" is meant that surface of the substrate that, in use, would be in contact with bodily tissues or fluids. "Disposed over" may, however, also refer to the application of the thin layer of material to an intervening layer that has been applied to the substrate, wherein the material is applied in such a manner that, were the intervening layer not present, the material would cover substantially the entire exposed surface of the substrate.

As used herein, "drug reservoir layer" refers either to a layer of one or more therapeutic agents applied neat or to a layer of polymer or blend of polymers that has dispersed within its three-dimensional structure one or more therapeutic agents. A polymeric drug reservoir layer is designed such that, by one mechanism or another, e.g., without limitation, by elution or as the result of biodegradation of the polymer, the therapeutic substance is released from the layer into the surrounding environment. For the purpose of this invention, the drug reservoir layer also acts as rate-controlling layer. As used herein, "rate-controlling layer" refers to a polymer layer that controls the release of therapeutic agents or drugs into the environment. While any thermoplastic acrylate or methacrylate polymer may be used to construct a drug reservoir layer of this invention, particularly useful polymers include, but not limited to, poly(n-butyl methacrylate) (PBMA). However, a limitation of PBMA is that it can have to low a drug permeability. Drug permeability may be increased by the introduction of polar groups.

As used herein, a "polar group" refers to a group in which the center of negative charge does not coincide with the center of position charge due to differing electronegativities of the atoms comprising the group. For the purposes of this invention, a polar group is intended to increase the overall polarity of the polymer which will increase the equilibrium water absorption, and thus, increase the drug permeability.

While any polar moiety that does not adversely affect the physical or chemical characteristics required of a polymer used as a coating on an implantable medical device may be used to construct a drug reservoir layer of this invention, a presently preferred polar group is alkyl ether. As used herein, "alkyl ether" refers to an unsaturated or saturated, branched- or straight-chain aliphatic group in which one or more of the carbon atoms in the chain are replaced by oxygen atoms. Examples of alkyl ethers useful for the purposes of this invention include, without limitation;

2-Methoxyethyloxy   2-Ethoxyethyloxy   1-Methyl-2-methoxyethyloxy

Poly (2methoxyethylacrylate) is known, and is used in blood oxygenators as a non-fouling polymer. The polar group 1-methyl-2-methoxyethyloxy- when placed on an acrylate results in a monomer that if hydrolysis occurs to the acrylate ester in vivo releases a very benign compound, 1-methoxy-2-propanol. These polyacrylates with alkyl ethers are quite polar, but have a Tg near room temperature so they will not be brittle.

Another presently preferred polar group is the amide moiety. Amide groups will not elevate the dry Tg (embrittling the polymer) as much as a polar moiety containing a hydroxyl group. They can also mimic the R-groups of the amino acids glutamine and asparagine which contain an amide group. Thus, they may be considered peptido-mimetic. Two of these compounds are lactamide and glycinamide which are biocompatible. Examples of amides useful for the purposes of this invention include, without limitation:

Acrylate/methacrylate copolymer of the drug reservoir layer can be formed by selecting a polar group which enhances adhesion of the layer to the phosphoryl choline acrylate polymer of the topcoat layer, and which also effectively controls the drug release rate. The ratio of monomers is selected to give a Tg when dry in the range of 0° C. to 70° C. When hydrated, the Tg should be in the range of −30° C. to 37° C. Some representative examples of non-polar monomers to copolymerize with the polar acrylate include, but are not limited to, methyl methacrylate, ethyl methacrylate, n-propyl methacrylate, isopropyl methacrylate, n-butyl methacrylate, isobutyl methacrylate, sec-butyl methacrylate, 2-ethyl-hexyl methacrylate, n-hexyl methacrylate, cyclohexyl methacrylate, n-hexyl methacrylate, isobornyl methacrylate, trimethylcyclohexyl methacrylate, methyl acrylate, ethyl arylate, n-propyl acrylate, isopropyl acrylate, n-butyl acrylate, isobutyl acrylate, sec-butyl acrylate, pentyl acrylate, n-hexyl acrylate, cyclohexyl acrylate, and combinations thereof.

As used herein, "therapeutic agent" refers to any substance that, when administered in a therapeutically effective amount to a patient suffering from a disease, has a therapeutic beneficial effect on the health and well-being of the patient. A therapeutic beneficial effect on the health and well-being of a patient includes, but it not limited to: (1) curing the disease; (2) slowing the progress of the disease; (3) causing the disease to retrogress; or, (4) alleviating one or more symptoms of the disease. As used herein, a therapeutic agent also includes any substance that when administered to a patient, known or suspected of being particularly susceptible to a disease, in a prophylactically effective amount, has a prophylactic beneficial effect on the health and well-being of the patient. A prophylactic beneficial effect on the health and well-being of a patient includes, but is not limited to: (1) preventing or delaying on-set of the disease in the first place; (2) maintaining a disease at a retrogressed level once such level has been achieved by a therapeutically effective amount of a substance, which may be the same as or different from the substance used in a prophylactically effective amount; or, (3) preventing or delaying recurrence of the disease after a course of treatment with a therapeutically effective amount of a substance, which may be the same as or different from the substance used in a prophylactically effective amount, has concluded.

As used herein, the terms "drug" and "therapeutic agent" are used interchangeably.

As used herein, "treating" refers to the administration of a therapeutically effective amount of a therapeutic agent to a patient known or suspected to be suffering from a vascular disease. A "therapeutically effective amount" refers to that amount of a therapeutic agent that will have a beneficial affect, which may be curative or palliative, on the health and well-being of the patient with regard to the vascular disease with which the patient is known or suspected to be afflicted. A therapeutically effective amount may be administered as a single bolus, as intermittent bolus charges, as short, medium or long term sustained release formulations or as any combination of these. As used herein, short-term sustained release refers to the administration of a therapeutically effective amount of a therapeutic agent over a period from about several hours to about 3 days. Medium-term sustained release refers to administration of a therapeutically effective amount of a therapeutic agent over a period from about 3 day to about 14 days and long-term refers to the delivery of a therapeutically effective amount over any period in excess of about 14 days.

As used herein, a "vascular disease" refers to a disease of the vessels, primarily arteries and veins, which transport blood to and from the heart, brain and peripheral organs such as, without limitation, the arms, legs, kidneys and liver. In particular "vascular disease" refers to the coronary arterial system, the carotid arterial system and the peripheral arterial system. The disease that may be treated is any that is amenable to treatment with a therapeutic agent, either as the sole treatment protocol or as an adjunct to other procedures such as surgical intervention. The disease may be, without limitation, atherosclerosis, vulnerable plaque, restenosis or peripheral arterial disease.

"Atherosclerosis" refers to the depositing of fatty substances, cholesterol, cellular waste products, calcium and fibrin on the inner lining or intima of an artery. Smooth muscle cell proliferation and lipid accumulation accompany the deposition process. In addition, inflammatory substances that tend to migrate to atherosclerotic regions of an artery are thought to exacerbate the condition. The result of the accumulation of substances on the intima is the formation of fibrous (atheromatous) plaques that occlude the lumen of the artery, a process called stenosis. When the stenosis becomes severe enough, the blood supply to the organ supplied by the particular artery is depleted resulting is strokes, if the afflicted artery is a carotid artery, heart attack if the artery is a coronary artery or loss of organ function if the artery is peripheral.

"Restenosis" refers to the re-narrowing or blockage of an artery at or near the site where angioplasty or another surgical procedure was previously performed to remove a stenosis. It is generally due to smooth muscle cell proliferation and, at times, is accompanied by thrombosis. Prior to the advent of implantable stents to maintain the patency of vessels opened by angioplasty, restenosis occurred in 40-50% of patients within 3 to 6 months of undergoing the procedure. Post-angioplasty restenosis before stents was due primarily to smooth muscle cell proliferation. These were also issues of acute reclosure due to vasospasm, dissection, and thrombosis at the site of the procedure. Stents eliminated acute closure from vasospasm and greatly reduced complications from dissections. While the use of IIb-IIIs anti-platelet drugs such as abciximab and epifabatide, which are anti-thrombotic, reduced the occurrence of post-procedure clotting (although stent placement itself can initiate thrombosis). Stent placement sites are also susceptible to restenosis due to abnormal tissue growth at the site of implantation. This form of restenosis tends also to occur at 3 to 6 months after stent placement but it is not affected by the use of anti-clotting drugs. Thus, alternative therapies are continuously being sought to mitigate, preferably eliminate, this type of restenosis. Drug eluting stents (DES) which release a variety of therapeutic agents at the site of stent placement have been in use for some time. To date these stents, comprised delivery interfaces (lengths) that are less than 40 mm in length and, in any event, have delivery interfaces that are not intended, and most often do not, contact the luminal surface of the vessel at the non-afflicted region at the periphery of the afflicted region.

"Vulnerable plaque" refers to an atheromatous plaque that has the potential of causing a thrombotic event and is usually characterized by a very thin wall separating it from the lumen of an artery. The thinness of the wall renders the plaque susceptible to rupture. When the plaque ruptures, the inner core of usually lipid-rich plaque is exposed to blood, with the potential of causing a potentially fatal thrombotic event through adhesion and activation of platelets and plasma proteins to components of the exposed plaque.

The phenomenon of "vulnerable plaque" has created new challenges in recent years for the treatment of heart disease. Unlike occlusive plaques that impede blood flow, vulnerable plaque develops within the arterial walls, but it often does so without the characteristic substantial narrowing of the arterial lumen which produces symptoms. As such, conventional methods for detecting heart disease, such as an angiogram, may not detect vulnerable plaque growth into the arterial wall.

The intrinsic histological features that may characterize a vulnerable plaque include increased lipid content, increased macrophage, foam cell and T lymphocyte content, and reduced collagen and smooth muscle cell (SMC) content. This fibroatheroma type of vulnerable plaque is often referred to as "soft," having a large lipid pool of lipoproteins surrounded by a fibrous cap. The fibrous cap contains mostly collagen, whose reduced concentration combined with macrophage-derived enzyme degradation can cause the fibrous cap of these lesions to rupture under unpredictable circumstances. When ruptured, the lipid core contents, thought to include tissue factor, contact the arterial bloodstream, causing a blood clot to form that can completely block the artery resulting in an acute coronary syndrome (ACS) event. This type of atherosclerosis is coined "vulnerable" because of unpredictable tendency of the plaque to rupture. It is thought that hemodynamic and cardiac forces, which yield circumferential stress, shear stress, and flexion stress, may cause disruption of a fibroatheroma type of vulnerable plaque. These forces may rise as the result of simple movements, such as getting out of bed in the morning, in addition to in vivo forces related to blood flow and the beating of the heart. It is thought that plaque vulnerability in fibroatheroma types is determined primarily by factors which include: (1) size and consistency of the lipid core; (2) thickness of the fibrous cap covering the lipid core; and (3) inflammation and repair within the fibrous cap.

"Thrombosis" refers to the formation or presence of a blood clot (thrombus) inside a blood vessel or chamber of the heart. A blood clot that breaks off and travels to another part of the body is called an embolus. If a clot blocks a blood vessel that feeds the heart, it causes a heart attack. If a clot blocks a blood vessel that feeds to brain, it causes a stroke.

Peripheral vascular diseases are generally caused by structural changes in blood vessels caused by such conditions as inflammation and tissue damage. A subset of peripheral vascular disease is peripheral artery disease (PAD). -PAD is a condition that is similar to carotid and coronary artery disease in that it is caused by the buildup of fatty deposits on the lining or intima of the artery walls. Just as blockage of the carotid artery restricts blood flow to the brain and blockage of the coronary artery restricts blood flow to the heart, blockage of the peripheral arteries can lead to restricted blood flow to the kidneys, stomach, arms, legs and feet.

Suitable therapeutic agents include, without limitation, antiproliferative agents, anti-inflammatory agents, antineoplastics and/or antimitotics, antiplatelet, anticoagulant, antifibrin, and antithrombin drugs, cytostatic or antiproliferative agents, antibiotics, antiallergic agents, antioxidants and other bioactive agents known to those skilled in the art.

Suitable antiproliferative agents include, without limitation, actinomycin D, or derivatives or analogs thereof, i.e., actinomycin D is also known as dactinomycin, actinomycin IV, actinomycin $I_1$, actinomycin $X_1$, and actinomycin $C_1$. Antiproliferative agents can be natural proteineous agents such as a cytotoxin or a synthetic molecule, all taxoids such as taxols, docetaxel, and paclitaxel, paclitaxel derivatives, all olimus drugs such as macrolide antibiotics, rapamycin, everolimus, structural derivatives and functional analogues of rapamycin, structural derivatives and functional analogues of everolimus, FKBP-12 mediated mTOR inhibitors, biolimus, perfenidone, prodrugs thereof, co-drugs thereof, and combinations thereof. Representative rapamycin derivatives and analogs include 40-O-(2; -hydroxyethyl)rapamycin (EVEROLIMUS®), 40-O-(3hydroxypropyl)rapamycin, 40-O-[2-(2-hydroxy)ethoxy]ethyl-rapamycin, 40-O-tetrazolylrapamycin, or 40-epi-(N1-tetrazolyl)-rapamycin, prodrugs thereof, co-drugs thereof, and combinations thereof.

Suitable anti-inflammatory agents include, without limitation, steroidal anti-inflammatory agents, a nonsteroidal anti-inflammatory agent, or a combination thereof. In some embodiments, anti-inflammatory agents include clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, morniflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof. The anti-inflammatory agent may also be a biological inhibitor of proinflammatory signaling molecules including antibodies to such biological inflammatory signaling molecules.

Suitable antineoplastics and/or antimitotics include, without limitation, paclitaxel, docetaxel, methotrexate, azathioprine, vincristine, vinblastine, fluorouracil, doxorubicin hydrochloride, and mitomycin.

Suitable antiplatelet, anticoagulant, antifibrin, and antithrombin drugs include, without limitation, sodium heparin, low molecular weight heparins, heparinoids, hirudin, argatroban, forskolin, vapiprost, prostacyclin, prostacyclin dextran, D-phe-pro-arg-chloromethylketone, dipyridamole, glycoprotein IIb/IIIa platelet membrane receptor antagonist antibody, recombinant hirudin and thrombin, thrombin inhibitors such as Angiomax ä (Biogen, Inc., Cambridge, Mass.), calcium channel blockers (such as nifedipine), colchicine, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6, 6-tetramethylpiperidine-1-oxyl (4-amino-TEMPO), estradiol, anticancer agents, dietary supplements such as various vitamins, and a combination thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium.

Other bioactive substances or agents that may be appropriate include alpha-interferon, and genetically engineered epithelial cells.

Suitable cytostatic or antiproliferative agents include, without limitation, angiopeptin, angiotensin converting enzyme inhibitors such as captopril, cilazapril or lisinopril, calcium channel blockers such as nifedipine; colchicine, fibroblast growth factor (FGF) antagonists; fish oil (ω-3-fatty acid); histamine antagonists; lovastatin, monoclonal antibodies such as, without limitation, those specific for Platelet-Derived Growth Factor (PDGF) receptors; nitroprusside, phosphodiesterase inhibitors, prostaglandin inhibitors, suramin, serotonin blockers, steroids, thioprotease inhibitors, triazolopyrimidine (a PDGF antagonist) and nitric oxide.

Suitable antiallergic agents include, without limitation, permirolast potassium. Other suitable bioactive agents include, without limitation, alpha-interferon, genetically engineered epithelial cells, dexamethasone and its derivatives, rapamycin derivatives and analogs such as 40-O-(2-hydroxyethyl)rapamycin (EVEROLIMUS®), 40-O-(3-hydroxypropyl)rapamycin, 40-O-[2-(2-hydroxyethoxy)]ethyl-rapamycin, and 40-O-tetrazolylrapamycin, synthetic inorganic and organic compounds, proteins and peptides, polysaccharides and other sugars, lipids, and DNA and RNA nucleic acid sequences having therapeutic, prophylactic or diagnostic activities, nucleic acid sequences include genes, antisense molecules which bind to complementary DNA to inhibit transcription, and ribozymes. Some other examples of suitable bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy; antiviral agents; analgesics and analgesic combinations; anorexics; antihelmintics; antiarthritics, antiasthmatic agents; anticonvulsants; antidepressants; antidiuretic agents; antidiarrheals; antihistamines; antimigrain preparations; antinauseants; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary; peripheral and cerebral; central nervous system stimulants; cough and cold preparations, including decongestants; hypnotics; immunosuppressives; muscle relaxants; parasympatholytics; psychostimulants; sedatives; tranquilizers; naturally derived or genetically engineered lipoproteins; and restenoic reducing agents.

Preferred therapeutic agents include corticosteroids, everolimus, zotarolimus, sirolimus, sirolimus derivatives, paclitaxel, bisphosphonates, ApoA1, mutated ApoA1, ApoA1 milano, ApoA1 mimetic peptides, ABC A1 agonists, anti-inflammatory agents, anti-proliferative agents, anti-angiogenic agents, matrix metalloproteinase inhibitors and tissue inhibitors of metalloproteinases.

As used herein, a "topcoat layer" refers to an outermost layer, that is, a layer that is in contact with the external environment and that is coated over all other layers. The topcoat layer may be applied to provide better hydrophilicity to the device, to better lubricate the device or merely as a physical protectant of the underlying layers. The topcoat layer comprises a phosphoryl choline acrylate polymer. The phosphoryl choline acrylate polymer moiety of the topcoat layer more specifically comprises poly(2-(methacryloyloxy-ethyl)-2-(trimethylammoniumethyl)-phosphate, inner salt)- co-(n-dodecylmethacrylate)-co-hydroxypropylmethacrylate)-co-(3-trimethoxysilyl)-propylmethacrylate), (PC1036® made by Biocompatibles UK Ltd.).

As used herein, "constitutional unit" refers to monomer component unit of the polymer moiety. The phosphoryl choline acrylate polymer has particularly designed to have 28.8 weight percentage of phosphoryl choline containing monomer which may have further crosslinking for strength. The (trimethylammoniumethyl)-phosphate, inner salt)/(n-dodcylmethacrylate)/(hydroxypropylmethacrylate)/(3-trimethoxysilyl)-propylmethacrylate) constitutional unit wt/wt ratio is from about 28.8:50.7:15.3:5.3.

As used herein, "substantial" or "substantially" refers to a condition that when modified by the word "substantially" is understood to not be necessarily absolute or perfect but would be considered close enough to those of ordinary skill in the art to warrant designating the condition as being present. Thus, for the purpose of this invention, a construct that exhibits at least 80% of a particular characteristic, preferably at least 90%, more preferably at least 95% and most preferably at present at least 99% of the full characteristic, the construct "substantially" exhibits the characteristic. Thus, the phosphoryl choline acrylate polymer of topcoat layer is substantially amorphous, if it is at least 80% amorphous.

Figure 2:
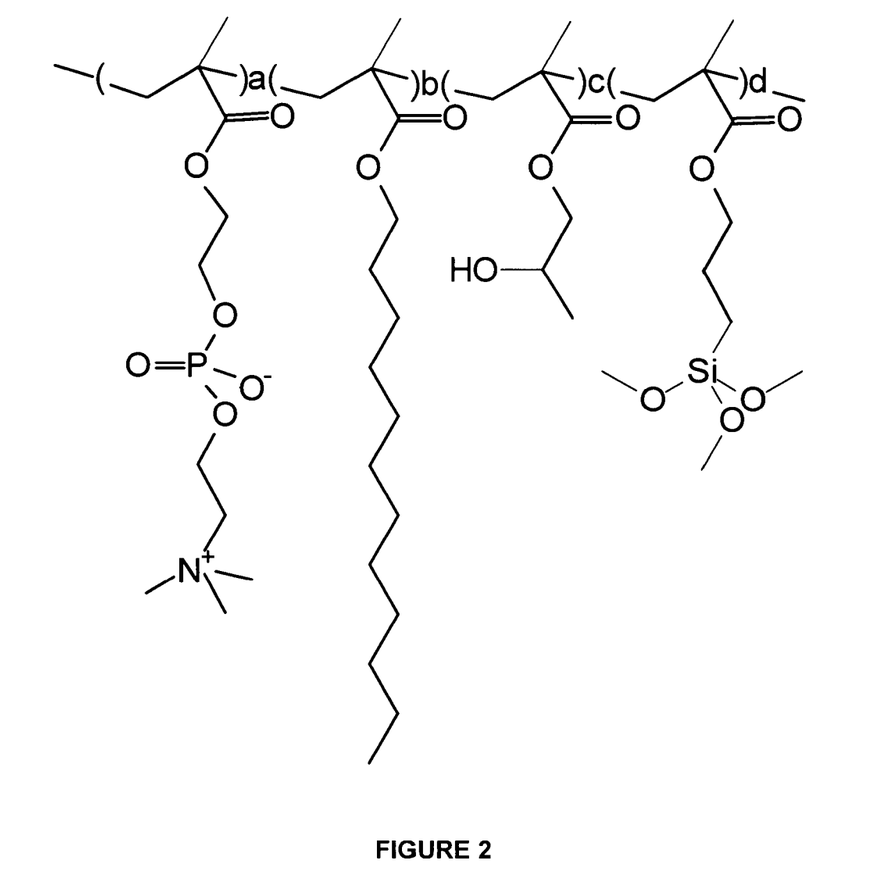
FIG. 2 depicts an embodiment of this invention showing the chemical structure of an exemplary phosphoryl choline acrylate polymer that may comprise a topcoat layer.

FIG. 2 depicts an embodiment of this invention showing chemical structure of phosphoryl choline acrylate polymer topcoat layer. The phosphoryl choline acrylate polymer topcoat has unique structure which includes phosphoryl choline, lauryl, isopropyl and silane moieties. The major advantage of the biocompatible phosphoryl choline acrylate polymer topcoat is its surface chemistry. Phosphoryl choline (PC) has a zwitterionic functionality that mimics the outer blood-contacting surface of the lipid bilayer structure in blood corpuscles. PC possesses numerous beneficial properties such as hemocompatibility, non-thrombogenicity, arterial tissue acceptance and long-term in vivo stability. PC has been used to increase biocompatibility of polymers, especially that of acrylic copolymers. The lauryl group improves the adhesion of topcoat layer with drug reservoir layer and fine tunes the amount of hydrophobicity on the polymer. The hydroxypropyl group improves coating integrity and mechanical properties. The silane moiety acts as a cross-linker.

Throughout the development of drug eluting stents, careful attention has been paid to their safety compared to bare metal stents. In all randomized clinical trials, the rates of stent thrombosis out to one year have been equivalent to those of bare metal stent controls. However, recent analysis has shown a trend for more late thrombosis at time frames beyond one year. Consequently, more attention is being placed on the issue of late, or very late, thrombosis. The phosphoryl choline acrylate polymer of the topcoat layer has all-acrylate backbone, synthetic polymer, which crosslinks to form a contiguous coating. PC has long been proposed to be a biocompatible polymer due to the biomimicry of the phosphoryl choline headgroup with the phospholipids found in cell membranes of erythrocytes and endothelial cells. An unexpected difference in the subacute thrombosis rates between two different types of stents was observed, namely, the stent which has a topcoat layer of phosphoryl choline acrylate polymer and the stent which does not have a topcoat layer. The adjudicated stent thrombosis rate at 2 years is statistically lower for stent which has a topcoat layer of PC containing polymer compared to the stent which does not have a topcoat layer. As both systems are based on the same stent, and were part of a randomized trial, it can be concluded that this unexpected result is due to either the presence of a drug, or the phosphoryl choline acrylate polymer in the topcoat layer, or both. It is known that the drug ABT-578 does not reduce the subacute stent thrombosis rate, which indicates that the phosphoryl choline acrylate polymer of the topcoat layer coating is a promising candidate for the lowering stent thrombosis rates. Nonetheless, the stent with topcoat layer of phosphoryl choline acrylate polymer demonstrates greater safety with regards to stent thrombosis.

What is claimed:
1. An implantable medical device, comprising:
a device body;
an optional primer layer disposed over the device body;
a drug reservoir layer disposed over the device body or the primer layer, if opted,
  wherein the drug reservoir layer comprises one or more therapeutic agents and poly(acrylate) or poly(methacrylate) of the formula:

wherein:
m = 0.005 to 0.90;
n = 0.10 to 0.995;
m + n = 1;
x = 65 to 6960;
$R_1$ and $R_2$ are independently selected from the group consisting of H and methyl;
Hydrocarbon Group is selected from the group consisting of an unsaturated or saturated, branched or straight chain $C_1$ to $C_{16}$ aliphatic, a cycloaliphatic, and an aromatic moiety; and
Polar Group is selected from the group consisting of and
a topcoat layer disposed as an outermost layer over the drug reservoir layer,
  wherein the topcoat layer comprises a phosphoryl choline acrylate polymer.
2. The implantable medical device of claim 1, wherein the device is a stent.
3. The implantable medical device of claim 1, wherein the phosphoryl choline acrylate polymer comprises poly(2-(methacryloyloxyethyl)-2-(trimethylammoniumethyl)- phosphate, inner salt)-co-(n-dodecylmethacrylate)-co-(hydroxypropylmethacrylate)-co-(3-trimethoxysilyl) propylmethacrylate).

4. The implantable medical device of claim 3, wherein the (2-(methacryloyloxyethyl)-2-(trimethylammoniumethyl)-phosphate, inner salt)/(n-dodecylmethacrylate)/ (hydroxypropylmethacrylate)/(3-trimethoxysilyl)propylmethacrylate) constitutional unit wt/wt ratio is about 28.8:50.7:15.3:5.3.

5. The implantable medical device of claim 1, wherein the phosphoryl choline acrylate polymer is substantially amorphous.

6. A method of treating a vascular disease, comprising:
deploying in the vasculature of a patient in need thereof an implantable medical device according to claim 1.

7. The method of claim 6, wherein the device is a stent.

8. The method of claim 6, wherein for the device, the phosphoryl choline acrylate polymer comprises poly(2-(methacryloyloxyethyl)-2-(trimethylammoniumethyl)-phosphate, inner salt)-co-(n-dodecylmethacrylate)-co-(hydroxypropylmethacrylate)-co-(3-trimethoxysilyl) propylmethacrylate).

9. The method of claim 8, wherein the (2-(methacryloyloxyethyl)-2-(trimethylammoniumethyl)-phosphate, inner salt)/(n-dodecylmethacrylate)/ (hydroxypropylmethacrylate)/(3-trimethoxysilyl)-propylmethacrylate) constitutional unit wt/wt ratio is about 28.8:50.7:15.3:5.3.

10. The method of claim 6, wherein for the device, the phosphoryl choline acrylate polymer is substantially amorphous.

11. The method of claim 6, wherein the vascular disease is atherosclerosis.

12. The method of claim 6, wherein the vascular disease is restenosis.

13. The method of claim 6, wherein the vascular disease is vulnerable plaque.

14. The method of claim 6, wherein the vascular disease is peripheral vascular disease.

15. The method of claim 6, wherein the vascular disease is late stent thrombosis.

* * * * *